US008444616B1

(12) United States Patent
Roy

(10) Patent No.: US 8,444,616 B1
(45) Date of Patent: May 21, 2013

(54) EJACULATE COLLECTION SYSTEM

(76) Inventor: William Grant Roy, Largo, FL (US)

( * ) Notice: Subject to any disclaimer, the term of this patent is extended or adjusted under 35 U.S.C. 154(b) by 751 days.

(21) Appl. No.: 12/589,766

(22) Filed: Oct. 28, 2009

(51) Int. Cl.
*A61F 5/44* (2006.01)
*A61M 1/00* (2006.01)

(52) U.S. Cl.
USPC ............ 604/349; 604/317; 604/322; 604/540

(58) Field of Classification Search
USPC .......... 604/317, 346, 347, 349, 540, 322.346; 600/30, 37
See application file for complete search history.

(56) References Cited

U.S. PATENT DOCUMENTS 5,633,286 A 5/1997 Chen
5,782,818 A 7/1998 Shubin
5,807,360 A 9/1998 Shubin

*Primary Examiner* — Melanie Hand

(57) ABSTRACT

A generally cylindrical housing having interior and exterior surfaces has open front and open back ends separated by an axial length. An open cell polyurethane foam sleeve has a flat face positionable adjacent to the interior surface of the housing and an undulating face adjacent to the central axis of the housing.

6 Claims, 5 Drawing Sheets

FIG 1
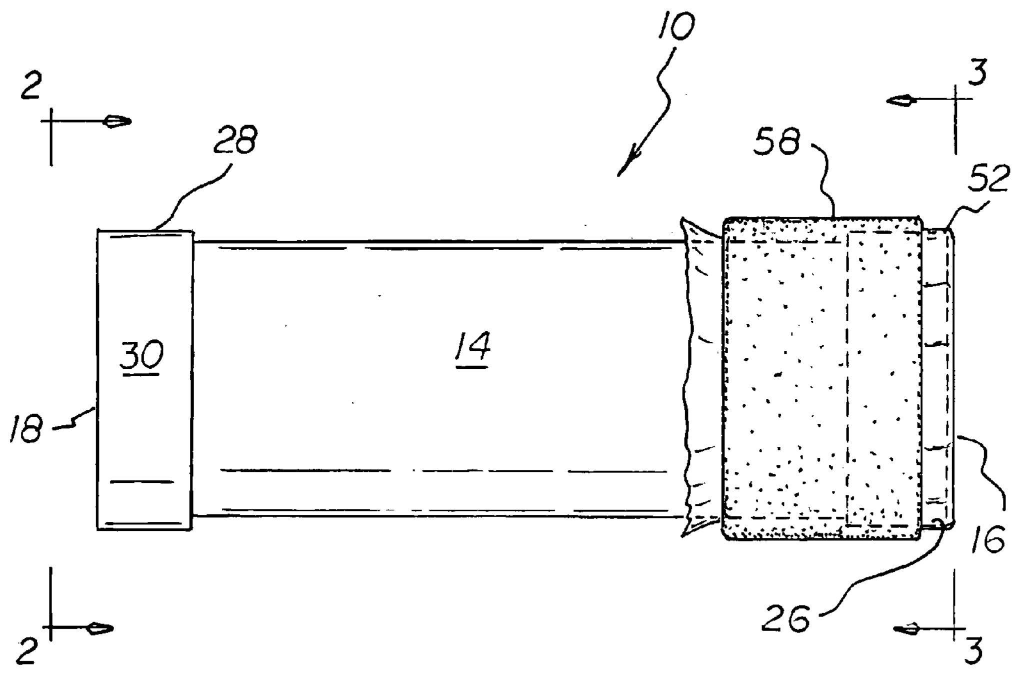
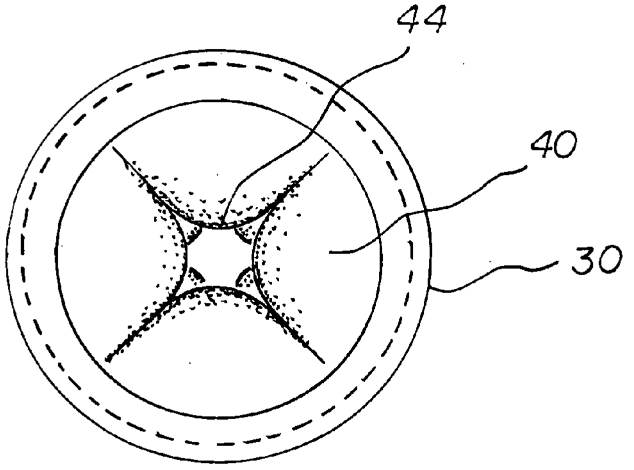
FIG 2

FIG 6
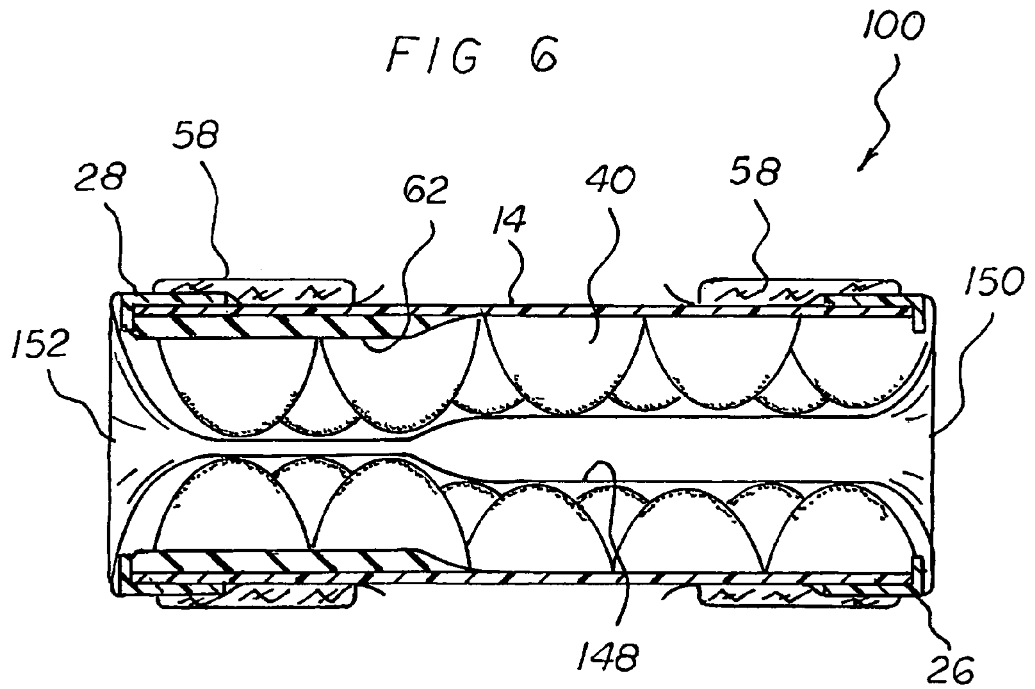
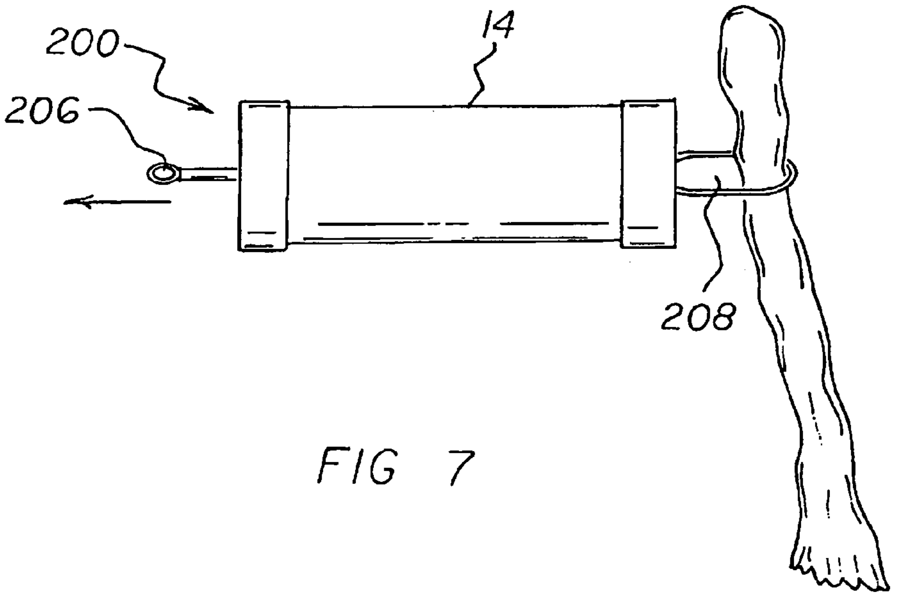
FIG 7

EJACULATE COLLECTION SYSTEM

BACKGROUND OF THE INVENTION

1. Field of the Invention

The present invention relates to an ejaculate collection system and more particularly pertains to effecting male orgasms and collecting ejaculate in a safe, sanitary, convenient and economical manner.

2. Description of the Prior Art

The use of ejaculate and sperm collection systems of known designs and configurations is known in the prior art. More specifically, ejaculate and sperm collection systems of known designs and configurations previously devised and utilized for the purpose of collecting ejaculate and sperm are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,633,286 issued May 27, 1997 to Chen relates to Gelatinous Elastomer Articles. U.S. Pat. No. 5,782,818 issued Jul. 21, 1998 to Shubin relates to a Device for Discreet Sperm Collection. Lastly, U.S. Pat. No. 5,807,360 issued Sep. 15, 1998 to Shubin related to a Device for Discreet Sperm Collection.

While these devices fulfill their respective, particular objectives and requirements, the aforementioned patents do not describe an ejaculate collection system that allows for effecting male orgasms and collecting ejaculate in a safe, sanitary, convenient and economical manner.

In this respect, the ejaculate collection system according to the present invention substantially departs from the conventional concepts and designs of the prior art, and in doing so provides an apparatus primarily developed for the purpose of effecting male orgasms and collecting ejaculate in a safe, sanitary, convenient and economical manner.

Therefore, it can be appreciated that there exists a continuing need for a new and improved ejaculate collection system which can be used for effecting male orgasms and collecting ejaculate in a safe, sanitary, convenient and economical manner. In this regard, the present invention substantially fulfills this need.

SUMMARY OF THE INVENTION

In view of the foregoing disadvantages inherent in the known types of ejaculate and sperm collection systems of known designs and configurations now present in the prior art, the present invention provides an improved ejaculate collection system. As such, the general purpose of the present invention, which will be described subsequently in greater detail, is to provide a new and improved ejaculate collection system and method which has all the advantages of the prior art and none of the disadvantages.

To attain this, the present invention essentially comprises a housing in a generally cylindrical configuration. The housing has a central axis bounded by an open circular front end and an open circular back end spaced by an axial length of 9 inches, plus or minus 10 percent. The housing has a circular cross section with an interior surface and an exterior surface. The interior surface has an interior diameter of 3 inches, plus or minus 10 percent. The open front and back ends allow entry from both ends. The housing is fabricated of an essentially rigid plastic material, preferably polyvinyl chloride.

Next provided are two similarly configured rings. The rings are a front ring push fit frictionally secured to the front end of the housing and a rear ring push fit frictionally secured to the back end of the housing. Each ring has a cylindrical section with an exposed exterior surface. The cylindrical section also has an interior surface overlying the exterior surface of the housing. Each ring has a radial section extending toward the central axis. Removal of the rings allows for the removal of the inner foam as for cleaning. The length of the cylindrical section of each ring is between 5 and 15 percent of the axial length of the housing. The radial length of each radial section is between 45 percent and 55 percent of the axial length of the axial section. The rings are fabricated of an essentially rigid low density plastic material, preferably polyethylene.

A sleeve is next provided. The sleeve has an interior diameter. The sleeve has a flat face positioned adjacent to the interior surface of the housing and an undulating face adjacent to the central axis. The maximum thickness of the sleeve is between 45 percent and 49 percent of the interior diameter of the sleeve. The sleeve is fabricated of an open cell polyurethane foam making it machine washable, the sleeve being in a rolled up state during use. The open cell foam allows for varying elasticity and density which results in varying pressure.

A flexible bag is next provided. The flexible bag has a closed end and an open end. The length of the bag between the open and closed ends is greater than the axial length of the housing. The open end of the bag is folded back over the open end of the housing. The closed end extends through and beyond the back end of the housing. The length of the bag within the housing receives and collects ejaculate when a penis is inserted into the open end of the bag while within the sleeve in response to axial reciprocation of the housing. The bag is fabricated of a flexible polyethylene sheet.

A flexible band is next provided. The flexible band is in a cylindrical configuration having an axial length of between 20 percent and 30 percent of the axial length of the housing. The band has limited elasticity. The band is positionable over the exterior surface of the housing adjacent to the front end of the housing to contact and hold the open end of the bag in an operative position during use.

Next provided is an optional removable insert. The removable insert is in a generally cylindrical configuration with an inner end and an outer end. The insert has an inner face and an outer face. The outer face is in contact with the interior surface of the housing adjacent to the back end. The inner face is in contact with the sleeve adjacent to the back end of the housing. The insert has an axial length of between 30 percent and 40 percent of the axial length of the housing. The insert reduces the interior diameter of the housing during use to accommodate smaller users. The insert is fabricated of a closed cell foam.

Lastly provided is a supplemental component. The supplemental component includes a wire bent to form a handle end with a small loop. The wire is further bent to form a bag-coupling end with a large loop. The supplemental component includes a linear central section with tape adjacent to the small loop and adjacent to the large loop. The central section has a length essentially equal to the length of the housing. The bag-coupling end and large loop are passed through the housing by a user grasping the handle end and the small loop. A sanitation-facilitating bag is inserted through the large loop. The user pulls the supplemental component and a portion of the bag back through the housing to facilitate sanitary use.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved ejaculate collection system which has all of the advantages of the prior art ejaculate and sperm collection systems of known designs and configurations and none of the disadvantages.

It is another object of the present invention to provide a new and improved ejaculate collection system which may be easily and efficiently manufactured and marketed.

It is further object of the present invention to provide a new and improved ejaculate collection system which is of durable and reliable constructions.

An even further object of the present invention is to provide a new and improved ejaculate collection system which is susceptible of a low cost of manufacture with regard to both materials and labor, and which accordingly is then susceptible of low prices of sale to the consuming public, thereby making such ejaculate collection system economically available to the buying public.

Even still another object of the present invention is to provide an ejaculate collection system for effecting male orgasms and collecting ejaculate in a safe, sanitary, convenient and economical manner, as for a soldier who has lost his hands and which system would be set up, used and cleaned by one with prostheses.

Lastly, it is an object of the present invention to provide a new and improved ejaculate collection system having a generally cylindrical housing with interior and exterior surfaces and open front and open back ends separated by an axial length. An open cell polyurethane foam sleeve has a flat face positionable adjacent to the interior surface of the housing and an undulating face adjacent to the central axis of the housing.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a side elevational view of an ejaculate collection system constructed ion accordance with the principles of the present invention.

FIG. 2 is a rear elevational view of the system taken along line 2-2 of FIG. 1.

FIG. 6 is a cross sectional view similar to FIG. 4 but illustrating an alternate embodiment of the invention.

FIG. 7 is a perspective illustration of the system of the prior Figures shown with a supplemental component for pulling a bag through the housing.

The same reference numerals refer to the same parts throughout the various Figures.

DESCRIPTION OF THE PREFERRED EMBODIMENT

Figure 3:
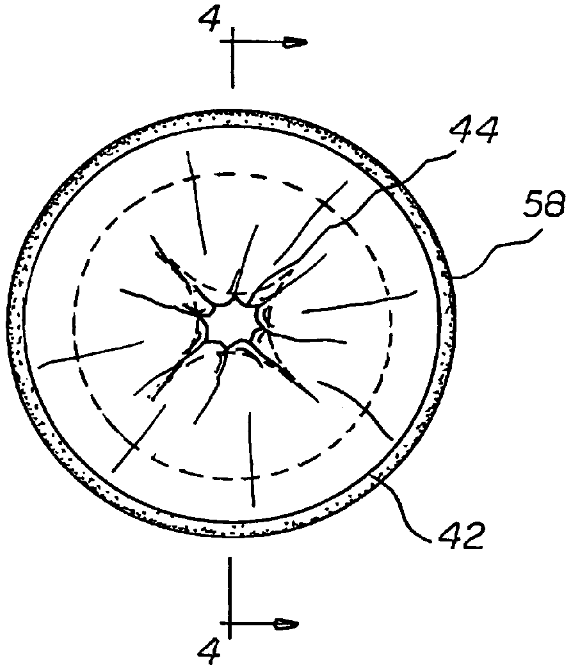
FIG. 3 is a front elevational view of the system taken along line 3-3 of FIG. 1.
Figure 4:
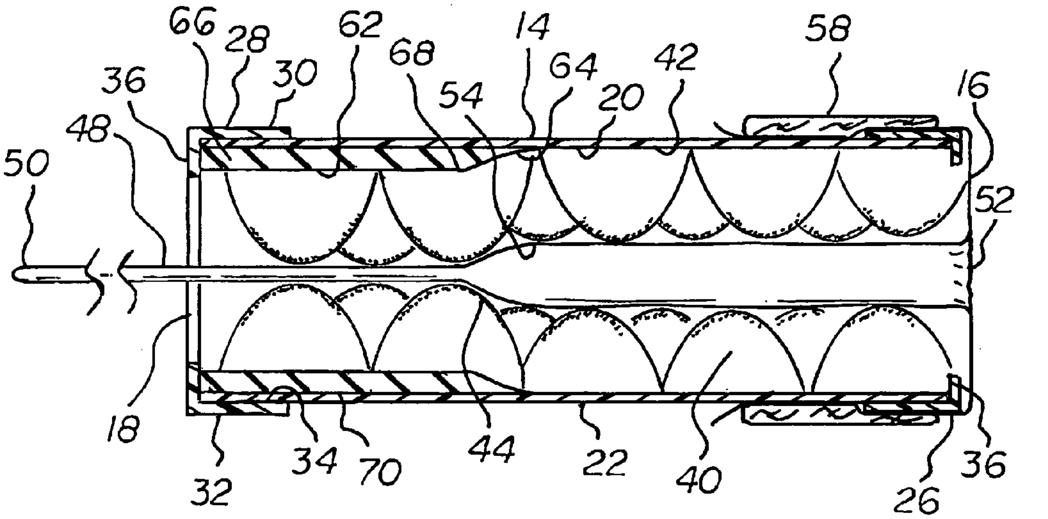
FIG. 4 is a cross sectional view of the system taken along line 4-4 of FIG. 3.
Figure 5:
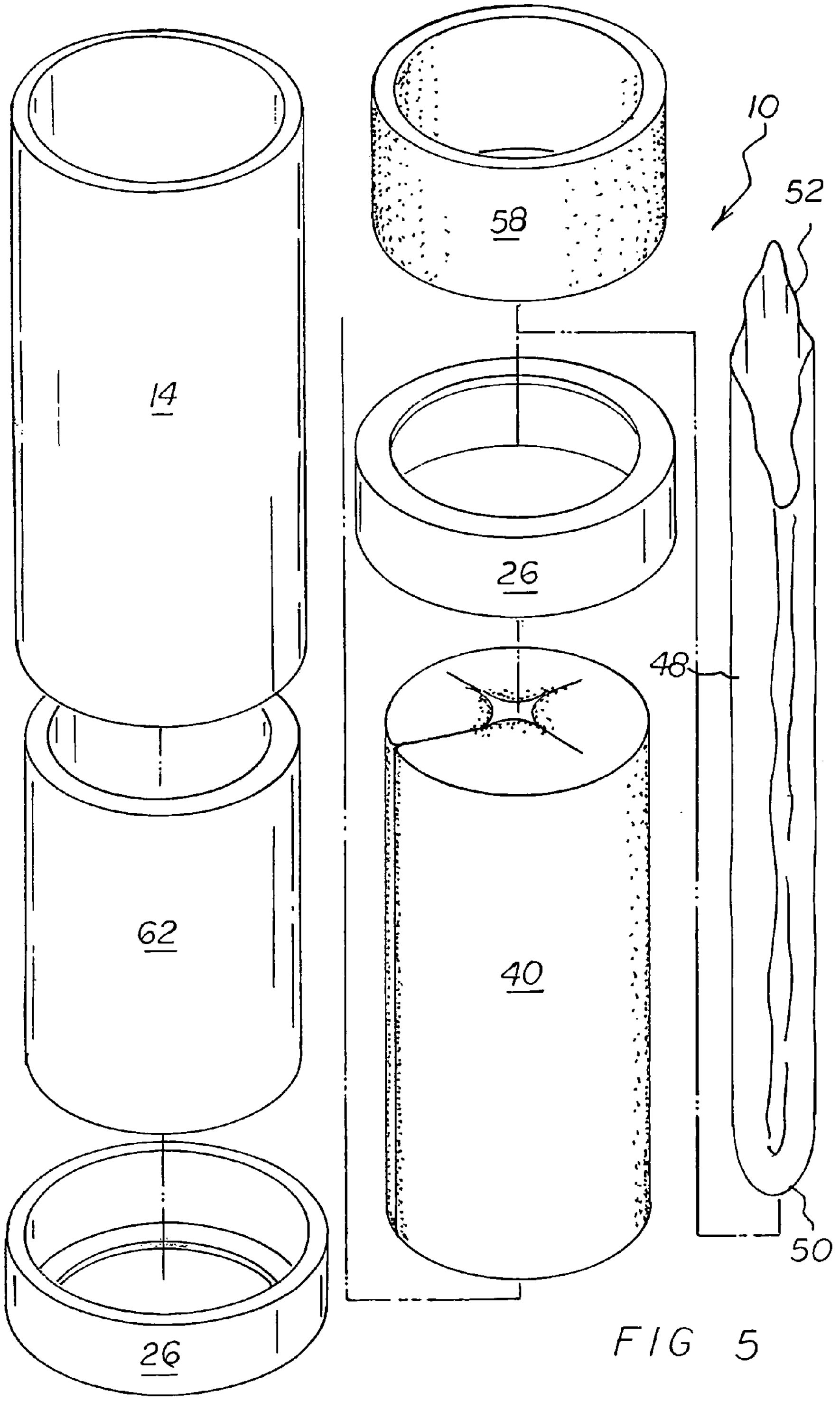
FIG. 5 is an exploded perspective view of the system shown in the prior Figures.
Figure 8:
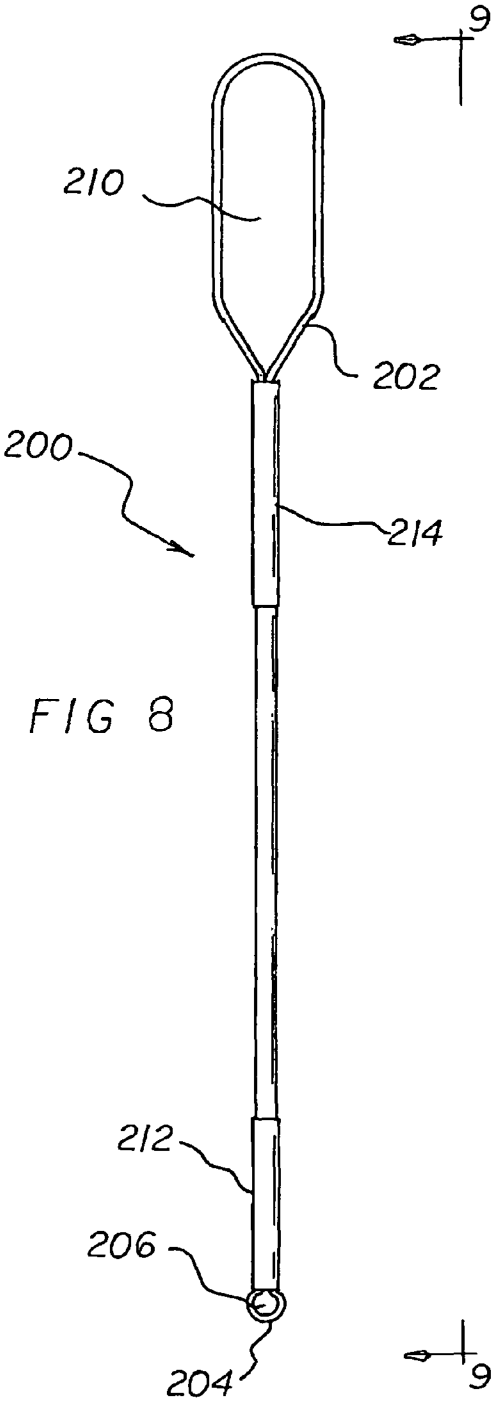
FIG. 8 is a front elevational view of the supplemental component of FIG. 7.
Figure 9:
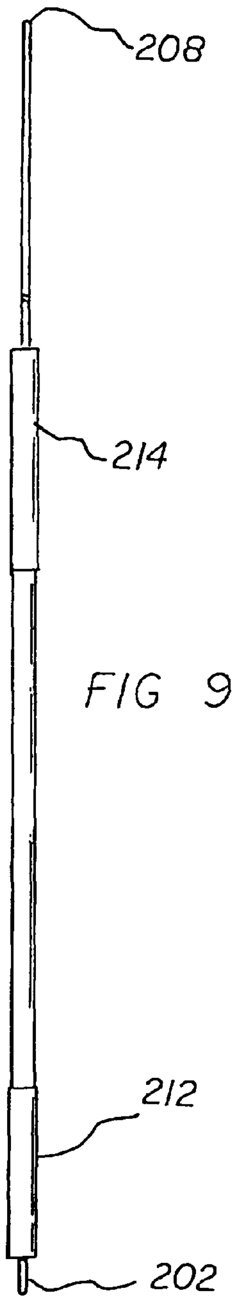
FIG. 9 is a side elevational view taken at line 9-9 of FIG. 8.

With reference now to the drawings, and in particular to FIG. 1 thereof, the preferred embodiment of the new and improved ejaculate collection system embodying the principles and concepts of the present invention and generally designated by the reference numeral 10 will be described.

The present invention, the ejaculate collection system 10 is comprised of a plurality of components. Such components in their broadest context include a housing and a sleeve. Such components are individually configured and correlated with respect to each other so as to attain the desired objective.

The ejaculate collection system 10 is for effecting male orgasms and for collecting the resulting ejaculate. The effecting and collecting being done in a safe, sanitary, convenient and economical manner. First provided is a housing 14 in a generally cylindrical configuration. The housing has a central axis bounded by an open circular front end 16 and an open circular back end 18 spaced by an axial length of 9 inches, plus or minus 10 percent. The housing has a circular cross section with an interior surface 20 and an exterior surface 22. The interior surface has an interior diameter of 3 inches, plus or minus 10 percent. The open front and back ends allow entry from both ends. The axial length of the housing is between 2.8 and 3.2 times the diameter of the housing. The housing is fabricated of an essentially rigid plastic material, preferably polyvinyl chloride.

Next provided are two similarly configured rings 26, 28. The rings are a front ring 26 push fit frictionally secured to the front end of the housing and a rear ring 28 push fit frictionally secured to the back end of the housing. Each ring has a cylindrical section 30 with an exposed exterior surface 32. The cylindrical section also has an interior surface 34 overlying the exterior surface of the housing. Each ring has a radial section 36 extending toward the central axis. Removal of the rings allows for the removal of the inner foam as for cleaning. The length of the cylindrical section of each ring is between 5 and 15 percent of the axial length of the housing. The radial length of each radial section is between 45 percent and 55 percent of the axial length of the axial section. The rings are fabricated of an essentially rigid low density plastic material, preferably polyethylene.

A sleeve 40 is next provided. The sleeve has an interior diameter. The sleeve has a flat face 42 positioned adjacent to the interior surface of the housing and an undulating face 44 adjacent to the central axis. The maximum thickness of the sleeve is between 45 percent and 49 percent of the interior diameter of the sleeve. The sleeve is fabricated of an open cell polyurethane foam making it machine washable, the sleeve being in a rolled up state during use. The open cell foam allows for varying elasticity and density which results in varying pressure.

A flexible bag 48 is next provided. The flexible bag has a closed end 50 and an open end 52. The length 54 of the bag between the open and closed ends is greater than the axial length of the housing. The open end of the bag is folded back over the open end of the housing. The closed end extends through and beyond the back end of the housing. The length of the bag within the housing receives and collects ejaculate when a penis is inserted into the open end of the bag while within the sleeve in response to axial reciprocation of the housing. The bag, in the preferred embodiment, is fabricated of a flexible polyethylene sheet. Although any type of bag may be utilized, the bag is preferably fabricated of a sanitary-facilitating material.

A flexible band 58 is next provided. The flexible band is in a cylindrical configuration having an axial length of between 20 percent and 30 percent of the axial length of the housing. The band has limited elasticity. The band is positionable over the exterior surface of the housing adjacent to the front end of the housing to contact and hold the open end of the bag in an operative position during use.

Next provided is an optional removable insert 62. The removable insert is in a generally cylindrical configuration with an inner end 64 and an outer end 66. The insert has an inner face 68 and an outer face 70. The outer face is in contact with the interior surface of the housing adjacent to the back end. The inner face is in contact with the sleeve adjacent to the back end of the housing. The insert has an axial length of between 30 percent and 40 percent of the axial length of the housing. The insert reduces the interior diameter of the housing during use to accommodate smaller users. The insert is fabricated of a closed cell foam like a swimming noodle.

An alternate embodiment of the invention is shown in FIG. 6. In this embodiment, the system further includes a flexible bag 148. The bag is fabricated of a flexible polyethylene sheet. The bag has an open first end 150 and an open second end 152. The length between the first and second ends is greater than the axial length of the housing. The first end is folded back over the open front end of the housing. The second end extends through and beyond the back end of the housing. The length of the bag within the housing receives and collects ejaculate when a penis is inserted into the open front end of the bag while within the sleeve. The receiving and collecting is in response to axial reciprocation of the housing.

The system of the present invention also includes a supplemental component 200. The supplemental component includes a wire 202 bent to form a handle end 204 with a small loop 206. The wire is further bent to form a bag-coupling end 208 with a large loop 210. The supplemental component includes a linear central section 212 with tape 214, 216 adjacent to the small loop and adjacent to the large loop. The central section has a length essentially equal to the length of the housing. The bag-coupling end and large loop are passed through the housing by a user grasping the handle end and the small loop. A sanitation-facilitating bag is inserted through the large loop. The user pulls the supplemental component and a portion of the bag back through the housing to facilitate sanitary use. Either the central extent of the bag or its periphery may be may be inserted through the large loop and passed through the housing at the discretion of the user.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An ejaculate collection system comprising:

a housing in a generally cylindrical configuration with a central axis, the housing having open front and open back ends separated by an axial length, the housing having an interior and exterior surcharge;

a sleeve having a flat face positionable adjacent to the interior surface of the housing, the sleeve having an undulating face adjacent to the central axis, the sleeve being fabricated of an open cell polyurethane foam; and a flexible bag having a closed end and an open end and a length between the open and closed ends greater than the axial length of the housing, the open end being folded back over the front end of the housing, the closed end extending through and beyond the back end of the housing, the length of the bag within the housing adapted to receive and collect ejaculate when a penis is inserted into the front end of the bag while within the sleeve, the receiving and collecting being in response to axial reciprocation of the housing, the bag being fabricated of a flexible polyethylene sheet.

2. The system as set forth in claim 1 and further including:

a flexible band in a cylindrical configuration having an axial length of between 20 percent and 30 percent of the axial length of the housing, the band having limited elasticity and positionable over the exterior surface of the housing adjacent to the front end to contact and hold the open end of the bag in an operative position during use.

3. The system as set forth in claim 1 and further including:

an optional removable insert in a generally cylindrical configuration with an inner end and an outer end, the insert having an inner face and an outer face, the outer face being in contact with the interior surface of the housing adjacent to the back end, the inner face being in contact with the sleeve adjacent to the back end of the housing, the insert having an axial length of between 30 percent and 40 percent of the axial length of the housing, the insert adapted to reduce the interior diameter of the housing during use, the insert being fabricated of a closed cell foam.

4. The system as set forth in claim 1 wherein the axial length of the housing is between 2.8 and 3.2 times the diameter of the housing.

5. The system as set forth in claim 1 and further including a supplemental component, the supplemental component including a wire bent to form a handle end with a small loop, the wire bent to form a bag-coupling end with a large loop, the supplemental component including a linear central section with tape adjacent to the small loop and adjacent to the large loop, the central section having a length essentially equal to the length of the housing, the bag-coupling end and large loop adapted to be passed through the housing by a user grasping the handle end and the small loop; and wherein the bag is adapted to be inserted through the large loop, when the user pulls the supplemental component and a portion of the bag back through the housing to facilitate sanitary use.

6. An ejaculate collection system for effecting male orgasms and for collecting the resulting ejaculate, the system comprising, in combination:

a housing in a generally cylindrical configuration having a central axis bounded by an open circular front end and an open circular back end spaced by an axial length of 9 inches, plus or minus 10 percent, the housing having a circular cross section with an interior surface and an exterior surface, the interior surface having an interior diameter of 3 inches, plus or minus 10 percent, the open front and back ends allowing entry from both ends, the housing being fabricated of an essentially rigid plastic material;

two similarly configured rings including a front ring push fit frictionally secured to the front end of the housing and a rear ring push fit frictionally secured to the back end of the housing, each ring having a cylindrical section with an exposed exterior surface and an interior surface overlying the exterior surface of the housing, each ring having a radial section extending toward the central axis, the length of the cylindrical section of each ring being between 5 and 15 percent of the axial length of the housing, the radial length of each radial section being between 45 percent and 55 percent of the axial length of the axial section, the rings being fabricated of an essentially rigid low density plastic material;

a sleeve with an interior diameter, the sleeve having a flat face positioned adjacent to the interior surface of the housing and an undulating face adjacent to the central axis, the maximum thickness of the sleeve being between 45 percent and 49 percent of the interior diameter of the sleeve, the sleeve being fabricated of an open cell polyurethane foam making it machine washable;

a flexible bag having a closed end and an open end and having a length between the open and closed ends being greater than the axial length of the housing, the open end of the bag being folded back over the open end of the housing, the closed end extending through and beyond the back end of the housing, the length of the bag within the housing adapted to receive and collect ejaculate when a penis is inserted into the open end of the bag while within the sleeve in response to axial reciprocation of the housing, the bag being fabricated of a flexible polyethylene sheet;

a flexible band in a cylindrical configuration having an axial length of between 20 percent and 30 percent of the axial length of the housing, the band having limited elasticity and positionable over the exterior surface of the housing adjacent to the front end of the housing to contact and hold the open end of the bag in an operative position during use;

an optional removable insert in a generally cylindrical configuration with an inner end and an outer end, the insert having an inner face and an outer face, the outer face being in contact with the interior surface of the housing adjacent to the back end, the inner face being in contact with the sleeve adjacent to the back end of the housing, the insert having an axial length of between 30 percent and 40 percent of the axial length of the housing, the insert adapted to reduce the interior diameter of the housing during use to accommodate smaller users, the insert being fabricated of a closed cell foam; and a wire bent to form a handle end with a small loop, the wire bent to form a bag-coupling end with a large loop, the supplemental component including a linear central section with tape adjacent to the small loop and adjacent to the large loop, the central section having a length essentially equal to the length of the housing, the bag-coupling end and large loop adapted to be passed through the housing by a user grasping the handle end and the small loop, a sanitation-facilitating bag adapted to be inserted through the large loop, the user adapted to pull the supplemental component and a portion of the bag back through the housing to facilitate sanitary use.

* * * * *